United States Patent
Meier et al.

(10) Patent No.: US 6,509,375 B1
(45) Date of Patent: Jan. 21, 2003

(54) METHOD FOR INCREASING PRODUCTIVITY IN BREEDER HENS

(75) Inventors: Albert H. Meier, Baton Rouge, LA (US); John M. Wilson, Metairie, LA (US)

(73) Assignee: Cyncron Corporation, Teaneck, NJ (US)

( * ) Notice: Subject to any disclaimer, the term of this patent is extended or adjusted under 35 U.S.C. 154(b) by 0 days.

(21) Appl. No.: 09/482,489

(22) Filed: Jan. 13, 2000

Related U.S. Application Data

(60) Provisional application No. 60/115,936, filed on Jan. 14, 1999.

(51) Int. Cl.[7] .................. A61K 31/24; A61K 38/00; A61K 47/00; A23K 1/165
(52) U.S. Cl. .................. 514/538; 514/12; 424/439; 424/442
(58) Field of Search .................. 514/12, 538; 424/309, 424/439, 442

(56) References Cited

U.S. PATENT DOCUMENTS

| | | | |
|---|---|---|---|
| 4,241,082 A | 12/1980 | Baba et al. | 424/439 |
| 4,604,968 A * | 8/1986 | Christensen | |
| 4,610,883 A | 9/1986 | Laurent et al. | 424/154 |
| 4,625,728 A | 12/1986 | Schonberg | 128/395 |
| 4,765,337 A | 8/1988 | Schonberg | 128/395 |
| 4,818,531 A * | 4/1989 | Anderson | |
| 5,336,672 A | 8/1994 | Southern, Jr. et al. | 514/188 |
| 5,624,671 A | 4/1997 | Araki et al. | 424/195.1 |
| 5,665,375 A | 9/1997 | Meier et al. | 424/439 |

FOREIGN PATENT DOCUMENTS

| | | | |
|---|---|---|---|
| EP | 0 167 381 | 8/1986 | A61K/37/43 |

OTHER PUBLICATIONS

Lupanova, G.E., Farmakol Toksikol (Mosc), 1986, 49(2), 35–37 (abstract).

* cited by examiner

*Primary Examiner*—William R. A. Jarvis
*Assistant Examiner*—Vickie Kim
(74) *Attorney, Agent, or Firm*—Darby & Darby

(57) ABSTRACT

A method for increasing chick production by increasing the level of L-DOPA in the bloodstream of breeder hens is described. Chick production is increased by increasing rates of egg laying, fertility of laid eggs, and number of fertile eggs that hatch. Methods for reducing the effects of stress on egg laying by increasing the level of L-DOPA in the bloodstream of breeder hens are also described.

7 Claims, 3 Drawing Sheets

Effect of Treatment on Egg Production in Broiler/Breeder Hens

Egg Production During 3 Weeks Following Retreatment of Broiler/Breeder Hens

METHOD FOR INCREASING PRODUCTIVITY IN BREEDER HENS

CROSS-REFERENCE TO RELATED APPLICATIONS

This application claims priority pursuant to 35 U.S.C. 119 based upon Provisional Application Ser. No. 60/115,936 filed Jan. 14, 1999, the entire disclosure of which is hereby incorporated by reference.

BACKGROUND OF THE INVENTION

The demand for poultry has expanded considerably over the last decade, particularly in the United States, due to changes in eating habits by the population, resulting in increased consumption of foods which contain less fat and cholesterol. To meet this demand, the poultry industry has had to change from a small home industry to a large scale manufacturing industry. One of the main problems caused by such large scale production is decreased reproductive productivity caused by stressing of the hens which lay the eggs which are allowed to hatch into poultry for consumption. Stress can be caused by overcrowding, moving, handling, changes in environmental conditions, or fright, and is one of the main causes of the decline in productivity, i.e., number of fertile eggs laid and the number of fertile eggs that hatch to yield live chicks. As hens age, they also become less productive.

Thus, there is a need in the art for methods that will allow breeder hens to produce eggs at a high rate for a longer period of their lifetimes. Further there is also a need in the art for methods to alleviate or reverse the deleterious effects of stress on the rate of egg laying by breeder hens as well as on the number of fertile eggs that are laid and that subsequently hatch.

The present inventors have now surprisingly and unexpectedly discovered that it is possible to improve productivity in breeder hens in terms of egg production, number of fertile eggs laid, and rate of hatching by the administration of L-Dihydroxyphenylalanine (hereinafter L-DOPA) to female poultry which lay eggs for hatching, rather than consumption, (i.e., breeder hens) or compositions that increase the concentration of L-DOPA in the bloodstream of breeder hens.

Further, administering L-DOPA or compositions that increase the concentration of L-DOPA in the bloodstream to breeder hens following stress reduces the recovery time needed to achieve the same egg laying productivity rate present before the stress.

SUMMARY OF THE INVENTION

In a first aspect, the present invention is directed to a method for increasing egg production by breeder hens by administering an effective amount of L-DOPA, a drug that increases the amount of L-DOPA in the hen's bloodstream, or a combination thereof to the breeder hens.

In a second aspect, the present invention is directed to a method for increasing the hatch rate of fertile eggs from breeder hens by administering an effective amount of L-DOPA, a drug that increases the amount of L-DOPA in the animal's bloodstream, or a combination thereof to the breeder hens.

In a third aspect, the present invention is directed to a method for increasing chick production by breeder hens by administering an effective amount of L-DOPA, a drug that increases the amount of L-DOPA in the hen's bloodstream, or a combination thereof to the breeder hen.

In a fourth aspect, the present invention is directed to a method for increasing the feeding efficiency of chicks hatched from eggs laid by breeder hens by administering an effective amount of L-DOPA, a drug that increases the amount of L-DOPA in the hen's bloodstream, or a combination thereof to the breeder hens prior to the laying of the eggs from which the chicks hatch.

In yet another aspect, the present invention is directed to a method for reducing the recovery time needed to achieve the same rate of egg laying productivity in breeder hens which have been stressed as before the stress was applied.

DETAILED DESCRIPTION OF THE PREFERRED EMBODIMENT

Figure 1:
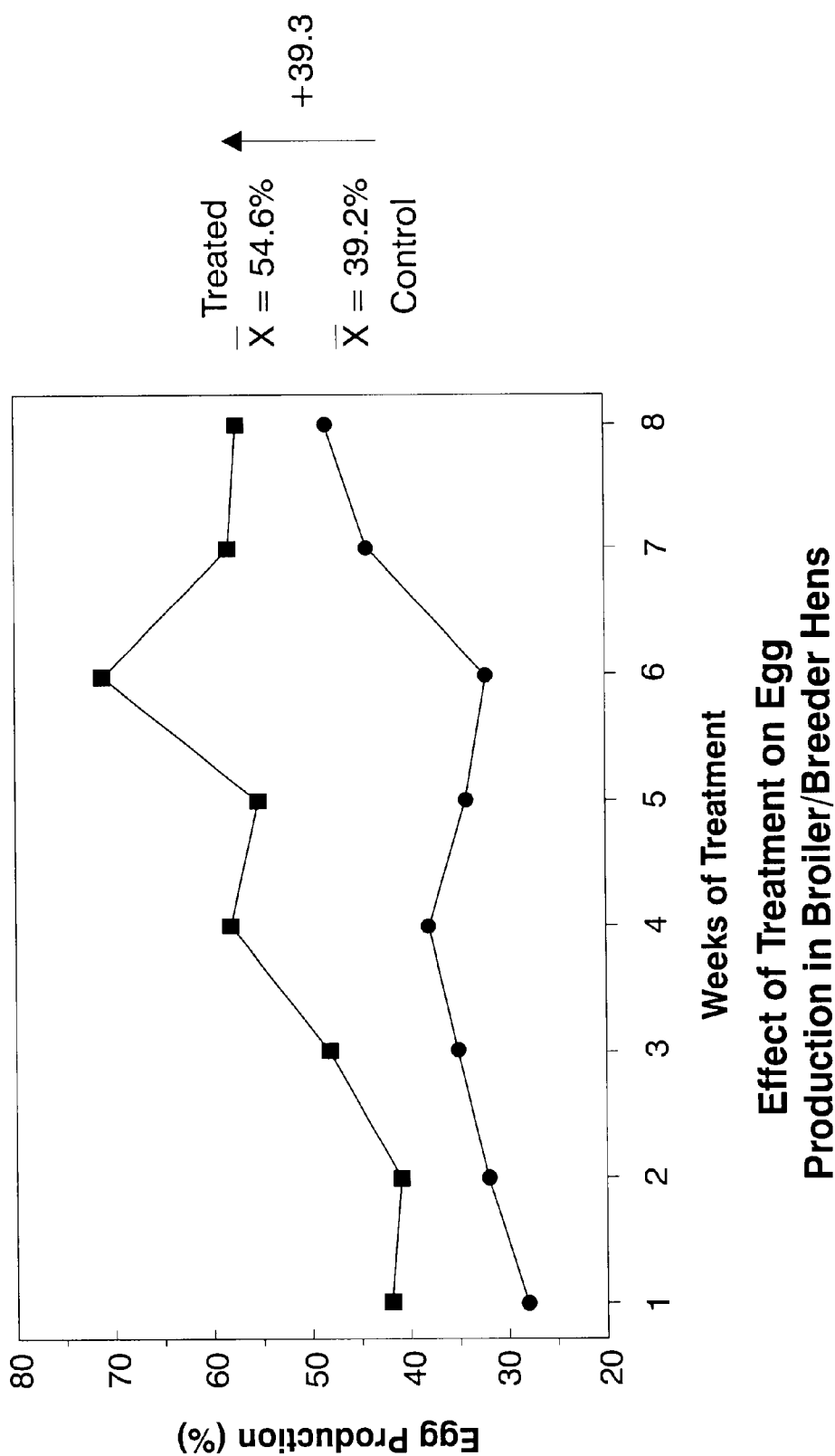
FIG. 1 is a graph that demonstrates that the average percentage egg production of L-DOPA treated broiler/breeder hens was greater than control hens over an eight week period.

Without limiting the scope of the invention, the preferred embodiment of the invention will be set forth. All patents, patent applications, and publications cited herein are incorporated by reference in their entirety. In case of conflict in terminology, the present specification controls.

It has been discovered by the inventors that elevating the level of the amino acid L-DOPA in the bloodstream of breeder hens has the effect of improving egg production and the rate of hatching of fertile eggs, and also increases the feeding efficiency of the chicks that hatch from eggs laid by treated breeder hens.

Further, elevating the level of L-DOPA in the bloodstream of poultry reduces the recovery time needed after a stress has been applied to achieve the same egg laying productivity rates that were present before the stress. The amino acid L-DOPA is a natural substance found in humans as well as animals, including poultry.

"L-DOPA", as used herein, is intended to include molecules containing substitutions in the chemical formula of L-DOPA not affecting the chemical activity and efficacy of the L-DOPA molecule in this application.

"An effective amount", as used herein, is intended to mean a quantity of L-DOPA which, when administered to a breeder hen, will cause an increase in egg production by the breeder hen, rate of hatching of fertile eggs from the breeder hen, decrease in time to recovery of egg laying productivity after stress by the breeder hen, or feeding efficiency in chicks that hatch from eggs laid by treated the breeder hen.

As used herein, "feeding efficiency" is defined as the ratio of the weight of feed necessary to achieve one weight unit in broiler/breeder hens.

The increase in productivity provided by the methods of the present invention are of significant benefit to the poultry industry, as it lowers the cost of chicken production.

The rates and amounts at which the L-DOPA can be administered in breeder hens to increase productivity according to the methods of the invention may be varied. A preferred dosage range of L-DOPA is between about 20 and about 300 mg/kg of body weight per day. A more preferred dosage range is between about 40 and about 150 mg/kg of body weight per day. The most preferred dosage is about 50 mg/kg of body weight per day.

The rates at which the L-DOPA can be administered may be varied. Additionally, one skilled in the art can vary the methods of administration. In the field, in actual service conditions, one skilled in the art can envision several methods by which L-DOPA can be administered to breeder hens. For example, one could administer conventional injections of the L-DOPA to the breeder hens. One could also administer timed-release subcutaneous implants or injections of L-DOPA.

Although the L-DOPA in the studies described in the Examples below was administered orally with animal feed, the beneficial effects are believed to be derived from an elevated L-DOPA level in the blood of breeder hens. As an alternative to administering L-DOPA orally to maintain increased levels of L-DOPA in the blood of breeder hens, drugs which inhibit the degradation of L-DOPA may also be administered and achieve the same effect. Examples of such drugs, known as dopa decarboxylase inhibitors, are carbidopa and benserazide, both of which have been used in conjunction with L-DOPA in the treatment of Parkinson's disease.

By using the aforementioned inhibitors, the amount of L-DOPA required to be administered can be reduced or eliminated resulting in a substantial economic savings. Also, food containing naturally occurring L-DOPA, e.g., broad beans, or drugs which stimulate L-DOPA synthesis may be administered to the breeder hens. Drugs which stimulate L-DOPA synthesis include, but are not limited to, tyrosine, phenylalanine, and inhibitors of the enzyme dopamine beta hydroxylase such as fusaric acid, disulfiram, and cysteamine, panthethine, phosphocysteamine, pantetheine, 3-pyridineacetic acid and 3-(3-pyridylmethoxycarbonyl)-propionic acid esters of pantethine and pantetheine, pantetheine-4'-phosphate, pharmaceutically acceptable salts thereof, and combinations thereof. Preferred dosages of such L-DOPA stimulating agents are from between about 50 and 500 mg/kg of body weight per day, preferably between about 100 and 200 mg/kg of body weight per day.

The present invention is intended to include any method by which the level of L-DOPA in breeder hens may be artificially elevated in order to increase the production of fertile eggs in breeder hens. It is also intended to include any method by which the level of L-DOPA in poultry is artificially elevated to reduce the recovery time of breeder hens following stress.

These effects have been verified in studies conducted by the inventors. The methodologies and results are described below.

EXAMPLE 1

20 Hubbard broiler/breeder hens and 4 roosters at 57 weeks of age were separated into two groups of 10 hens and two roosters. One group was fed a control (untreated) diet and the second group was fed the same diet supplemented with 50 mg/kg body weight of L-DOPA for 10 weeks. This was followed by a 3–4 week rest period and then treatment was initiated for another 3 weeks (retreatment).

Figure 2:
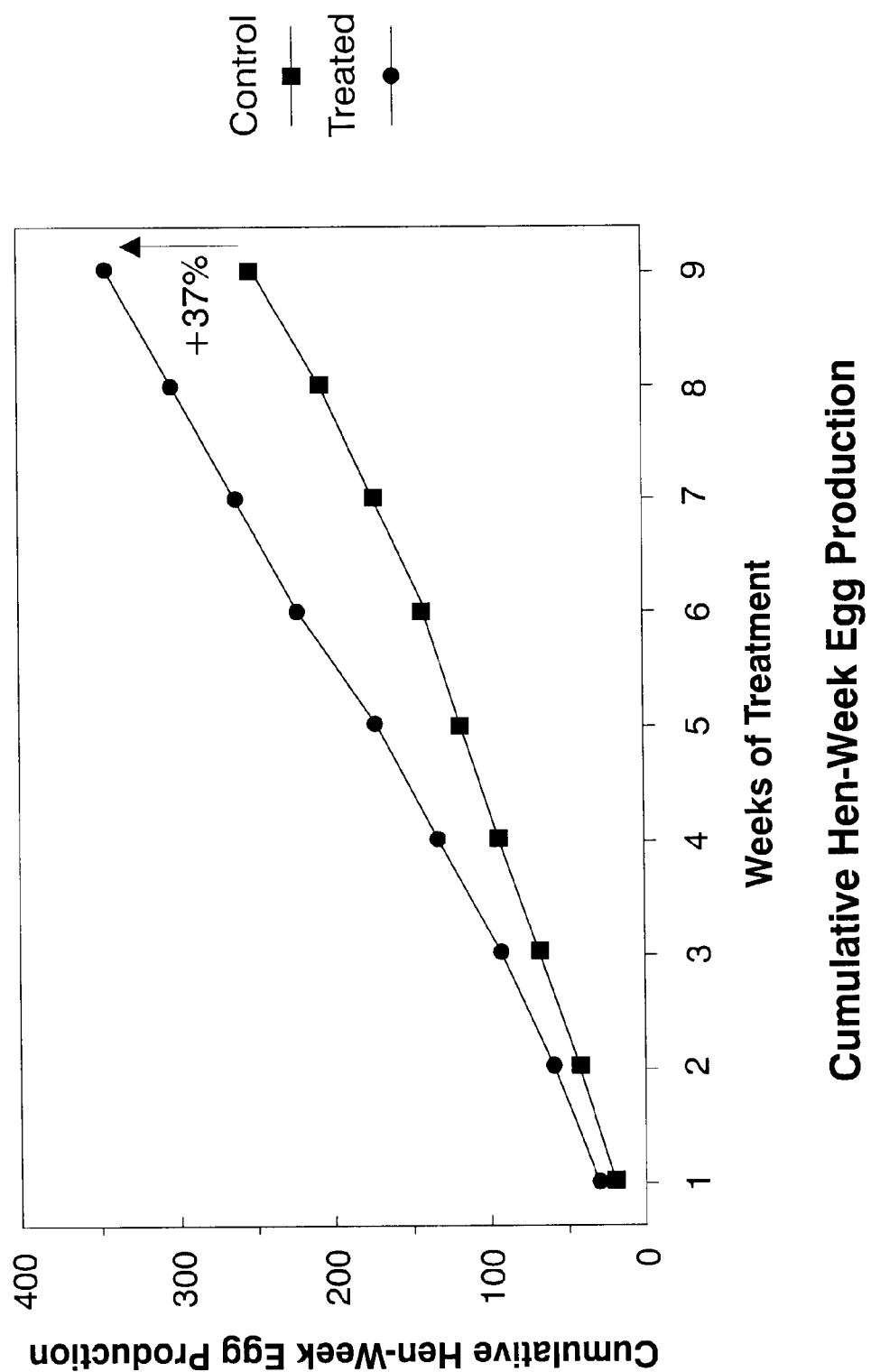
FIG. 2 is a graph that shows that the average weekly and cumulative egg production of L-DOPA treated broiler/breeder hens was significantly higher than control hens over a nine week period.
Figure 3:
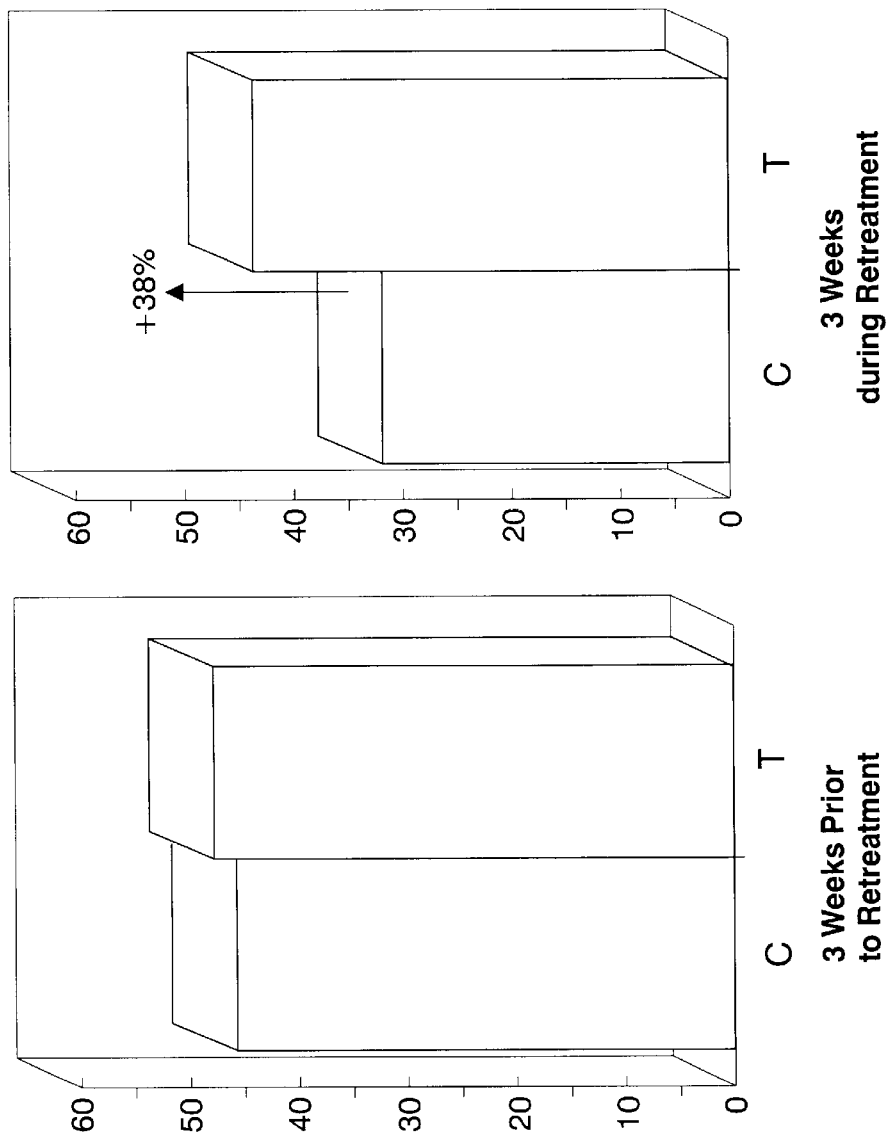
FIG. 3 is a graph that demonstrates that there is an increase in the percentage egg production in L-DOPA treated broiler/breeder hens compared to control hens during three weeks of re-treatment with L-DOPA following three weeks without L-DOPA.

As shown in FIGS. 1 and 2, average weekly egg production and cumulative egg production of broiler/breeder hens receiving L-DOPA-supplemented feed was significantly higher than the production of control hens. This was also the case during the 3 weeks of re-treatment following the 3 week rest period during which the treatment group was not administered L-DOPA (FIG. 3).

Beginning with week 6 of treatment, eggs from treated hens were incubated and hatched. The progeny were then followed for seven to eight weeks to assess weight gain and feeding efficiency. The results are shown in Table 1, below. Egg production percentage is in terms of eggs/day/100 hens. The fertility percentage is the number of eggs laid that are fertile. The hatch/fertile ratio is the number of fertile eggs that hatch divided by the number of fertile eggs laid. The chick production percentage is the product of the egg production, fertility, and hatch/fertile percentages.

TABLE 1

Chick production by control hens and hens treated with L-DOPA

| Week | Egg production (%) | Fertility (%) | Hatch/Fertile (%) | Chick Production (%) |
|---|---|---|---|---|
| L-DOPA TREATED BREEDER HENS | | | | |
| 7 | 71 | 84 | 75 | 45 |
| 8 | 58 | 100 | 90 | 52 |
| 10 | 62 | 92 | 86 | 55 |
| Mean | 64 | 92 | 84 | 51 |
| CONTROL BREEDER HENS | | | | |
| 7 | 32 | 83 | 76 | 20 |
| 8 | 45 | 91 | 74 | 30 |
| 10 | 62 | 90 | 69 | 38 |
| Mean | 46 | 88 | 73 | 29 |

The data set out in Table 1 show the significant increase in egg production, fertility and chick production in L-DOPA treated hens over controls. Fertile eggs set for incubation during weeks 7, 8 and 10 of treatment with L-DOPA had 15% higher rates of hatching over eggs from control hens. The increase in fertility and hatching rates combined with the increase in egg production resulted in an overall gain in chick production of 76% over the control groups.

The progeny chicks hatched from eggs laid by the control and L-DOPA treated breeder hens were evaluated for feeding efficiency, as described above. The results are set out in Table 2, below.

TABLE 2

Final feeding efficiency (pounds of feed consumed per pound of body weight gained) of progeny by treatment.

| Progeny | Group 1 | Group 2 | Group 3 | Group 4 | Group 5 | Average |
|---|---|---|---|---|---|---|
| Treated | 1.99 | 2.07 | 1.98 | 2.07 | 2.12 | 2.05 |
| Control | 2.26 | 2.21 | 2.07 | 2.11 | 2.22 | 2.18 |

Progeny Group 1: 8 week feed conversions; Week 8 of treatment in broiler breeders
Progeny Group 2: 8 week feed conversions; Week 7 of treatment in broiler breeders
Progeny Group 3: 8 week feed conversions; Week 8 of treatment in broiler breeders
Progeny Group 4: 7 week feed conversions; Week 9 of treatment in broiler breeders
Progeny Group 5: 6 week feed conversions; Week 10 of treatment in broiler breeders Table 2 shows a significant effect of L-DOPA administration on feeding efficiency of progeny of L-DOPA treated hens over control birds. The progeny of the treated hens hatched from eggs during weeks 6–10 of treatment had an average 6% increase in feeding efficiency relative to control birds.

EXAMPLE 2

58 week old broiler/breeder hens were obtained from a commercial private breeder when they were laying at a rate of approximately 54% (54 eggs/day/100 hens; 38 eggs/week/10 hens). Following handling and transfer of hens to new pens during hot weather, egg production was severely reduced by approximately 60%. L-DOPA was added to the feed of the treatment group of breeder hens at a dosage of 50 mg/day/kg body weight; none was added to the feed of the control group. Egg laying was monitored daily for 9 weeks in the treated and control group. The results are set out in Table 3, below.

TABLE 3

Effects of DOPA treatment on number of eggs laid by broiler breeder hens following handling and transfer stress.

| Treatment | Week | | | | | | | | | Total |
| --- | --- | --- | --- | --- | --- | --- | --- | --- | --- | --- |
| | 1 | 2 | 3 | 4 | 5 | 6 | 7 | 8 | 9 | |
| Control[1] | 20 | 23 | 25 | 27 | 24 | 23 | 31 | 34 | 43 | 250 |
| DOPA[1,2] | 10 | 29 | 34 | 41 | 39 | 50 | 41 | 40 | 43 | 327 |

[1]Ten hens/group
[2]DOPA provided in food (50 mg/day/kg body weight)

The results shown in Table 3 illustrate that during the nine weeks following the moving stress, the total number of eggs laid by hens treated with L-DOPA was 31% greater than that of untreated controls (327 eggs vs. 250).

It was also found that the recovery time of egg laying hens can be reduced from the two months necessary for control hens to achieve the same egg laying productivity rate before the stress, to one month in the L-DOPA treated hens.

The studies above were carried out on breeder hens. However, the present invention may be employed with any animal. Thus the method could be used to increase productivity or decrease stress in geese, ducks, turkeys, quail, swine, cattle, and any non-domestic animal that undergoes stress as a result of captivity. The method of the invention can also be employed to increase the feeding efficiency of progeny of such animals.

There are of course other alternate embodiments which are obvious from the foregoing descriptions of the invention which are intended to be included within the scope of the invention as defined by the following claims.

What is claimed is:

1. A method of increasing the hatch rate of fertile eggs laid by a breeder hen which comprises administering to said breeder hen an effective amount for increasing the hatch rate of fertile eggs laid by said breeder hen of L-Dihydroxyphenylalanine (L-DOPA), wherein said effective amount comprises between 20 and 300 mg/kg of body weight of L-DOPA per day.

2. The method of claim 1, wherein said effective amount comprises between 40 and 150 mg/kg of body weight of L-DOPA per day.

3. The method of claim 2 wherein said effective amount comprises about 50 mg/kg of body weight of L-DOPA per day.

4. The method of claim 3 wherein said effective amount of L-DOPA is administered orally.

5. The method of claim 4 which comprises administering said effective amount to said breeder hen by incorporating said effective amount in food to be fed to said breeder hen.

6. A method for increasing chick production by a breeder hen which comprises administering to said breeder hen an effective amount for increasing chick production by said breeder hen of L-Dihydroxyphenylalanine (L-DOPA), wherein said effective amount is between about 40 and 150 mg/kg of body weight per day.

7. The method of claim 6 wherein said effective amount of L-DOPA is administered orally.

* * * * *